(12) United States Patent
Delaney, Jr. et al.

(10) Patent No.: US 11,938,216 B2
(45) Date of Patent: Mar. 26, 2024

(54) INJECTABLE COMPOSITIONS

(71) Applicant: Boston Scientific Scimed, Inc., Maple Grove, MN (US)

(72) Inventors: Joseph T. Delaney, Jr., Minneapolis, MN (US); Samuel Raybin, Marlborough, MA (US); John Kummailil, Sherborn, MA (US); Matthew B. Hollyer, Williamstown, VT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 252 days.

(21) Appl. No.: 15/655,320

(22) Filed: Jul. 20, 2017

(65) Prior Publication Data

US 2018/0021252 A1   Jan. 25, 2018

Related U.S. Application Data

(60) Provisional application No. 62/365,205, filed on Jul. 21, 2016.

(51) Int. Cl.
| | | |
|---|---|---|
| *A61K 9/00* | (2006.01) | |
| *A61K 47/02* | (2006.01) | |
| *A61K 47/36* | (2006.01) | |
| *A61B 5/00* | (2006.01) | |
| *A61B 5/055* | (2006.01) | |
| *A61B 17/00* | (2006.01) | |
| *A61B 17/34* | (2006.01) | |
| *A61B 90/00* | (2016.01) | |

(52) U.S. Cl.
CPC ............ *A61K 9/0019* (2013.01); *A61K 47/02* (2013.01); *A61K 47/36* (2013.01); *A61B 5/055* (2013.01); *A61B 5/6842* (2013.01); *A61B 5/687* (2013.01); *A61B 5/6871* (2013.01); *A61B 5/6873* (2013.01); *A61B 2017/00269* (2013.01); *A61B 2017/00898* (2013.01); *A61B 2017/00942* (2013.01); *A61B 17/3478* (2013.01); *A61B 2090/3908* (2016.02); *A61B 2090/3933* (2016.02); *A61B 2090/3937* (2016.02)

(58) Field of Classification Search
CPC ......... A61K 9/0019; A61K 9/08; A61K 9/107
See application file for complete search history.

(56) References Cited

U.S. PATENT DOCUMENTS

| | | | |
|---|---|---|---|
| 6,319,260 B1 | 11/2001 | Yamamoto | |
| 6,562,632 B1 | 5/2003 | Szalecki et al. | |
| 6,689,616 B1 * | 2/2004 | Bosies | A61K 49/006 |
| | | | 436/161 |
| 7,748,388 B2 | 7/2010 | Yamamoto | |
| 2003/0225460 A1 | 12/2003 | Gostout et al. | |
| 2005/0031540 A1 * | 2/2005 | Nielsen | A61K 9/0048 |
| | | | 424/9.6 |
| 2007/0003525 A1 * | 1/2007 | Moehlenbruck | A61K 35/30 |
| | | | 424/93.7 |
| 2007/0071792 A1 * | 3/2007 | Varner | A61K 9/0024 |
| | | | 424/427 |
| 2010/0266716 A1 * | 10/2010 | Olson | A01N 35/02 |
| | | | 424/756 |
| 2012/0141379 A1 * | 6/2012 | Vogel | A61K 9/1635 |
| | | | 424/9.3 |
| 2015/0099928 A1 | 4/2015 | Smith et al. | |
| 2016/0067190 A1 * | 3/2016 | Anderson | A61K 9/0019 |
| | | | 424/489 |

FOREIGN PATENT DOCUMENTS

| | | | | |
|---|---|---|---|---|
| EP | 2783709 A1 | 10/2014 | | |
| GB | 2302094 A | 1/1997 | | |
| JP | 2001192336 | 7/2001 | | |
| JP | 2003527447 A | 9/2003 | | |
| JP | 2003528130 A | 9/2003 | | |
| JP | 2014185333 A | 10/2014 | | |
| WO | 0035490 A2 | 6/2000 | | |
| WO | 0172281 A2 | 10/2001 | | |
| WO | 2001072281 A2 | 10/2001 | | |
| WO | 20010172281 A2 | 10/2001 | | |
| WO | 9931183 A1 | 9/2003 | | |
| WO | 2013077357 A1 | 5/2013 | | |
| WO | 2013077357 A1 | 10/2014 | | |
| WO | 2015054208 A1 | 4/2015 | | |
| WO | WO-2015054208 A1 * | 4/2015 | ........... A61K 9/0031 | |
| WO | 2015075015 A1 | 5/2015 | | |

OTHER PUBLICATIONS

Kim et al (Conjugate polymer nanoparticles for biomedical in vivo imaging, Chem Comm, vol. 46, No. 10, Mar. 2010, pp. 1617-1619 (Year: 2010).*
Miki et al (Near-Infrared Dye-Conjugated Amphiphilic Hyaluronic Acid Derivatives as a Dual Contrast Agent for In Vivo Optical and Photoacoustic Tumor Imaging; Biomacromolecules, 16, 2015, 219-227). (Year: 2015).*
Dong et al., "Sulfur(VI) Fluoride Exchange (SuFEx): Another Good Reaction for Click Chemistry," Angew. Chem. Int. Ed., vol. 53, pp. 9430-9448 (2014).
Narayanan et al., "Sulfonyl fluorides as privileged warheads in chemical biology," Chemical Science, vol. 6, pp. 2650-2659, (2015).
Scaglione et al., "The Epidemiology of Cirrhosis in the United States A Population-based Study," J. Clin. Gastroenterol., vol. 49, No. 8, pp. 690-696 (2015).

(Continued)

*Primary Examiner* — Micah Paul Young
(74) *Attorney, Agent, or Firm* — Seager, Tufte & Wickhem, LLP

(57) ABSTRACT

The present disclosure relates to injectable compositions sterile injectable fluid compositions comprising a polysaccharide having a color in the visible spectrum, methods of forming the same, kits containing the same, and methods for performing agent-assisted procedures in a patient using the same.

15 Claims, 1 Drawing Sheet

(56) References Cited

OTHER PUBLICATIONS

Sarin et al., "Prevalence, Classification and Natural History of Gastric Varices: A Long-term Follow-up Study in 568 Portal Hypertension Patients," Hepatology, vol. 16, No. 6, pp. 1343-1349.
International Search Report and Written Opinion dated Oct. 26, 2017) for PCT/US2017/043123(18 pages).
Kim et al., "Conjugated polymer nanoparticles for biomedical in vivo imaging," Chem. Commun., vol. 46, No. 10, Jan. 1, 2010, pp. 1617-1619.
Kim, S., et al., "Conjugated polymernanoparticles for biomedical in vivo imaging", Chemical Communications 46(10):1617-1619 (2010).
International Preliminary Report on Patentability for PCT/US2017/043123, dated Jan. 22, 2019, 7 pages.
Miki, K. et al., "Near-Infrared Dye-Conjugated Amphiphilic Hyaluronic Acid Derivatives as a Dual Contrast Agent for In Vivo Optical and Photoacoustic Tumor Imaging" Biomacromolecules 2015, 16, 1, 219-227 Publication Date: Nov. 17, 2014.
Miki et al., "Near-Infrared Dye-Conjugated Amphiphilic Hyaluronic Acid Derivatives as a Dual Contrast Agent for In Vivo Optical and Photoacoustic Tumor Imaging", Biomacromolecules 2015, 16 1 219-227, 10 pages, Nov. 17, 2014. (Abstract Only).
Kim et al., "Conjugated Polymer Nanoparticles for Biomedical in VIVO Imaging", Chem. Commun., 2010, 46, 1617-1619, 6 pages.
Yasuda et al., "Hyaluronan as a Biomaterial", Aziz; 2003; Heldin, 2003, 1 page.
EP Communication Pursuant to Article 94 (3) EPC dated Apr. 14, 2023 for Application No. 17751166.4-1109.

\* cited by examiner

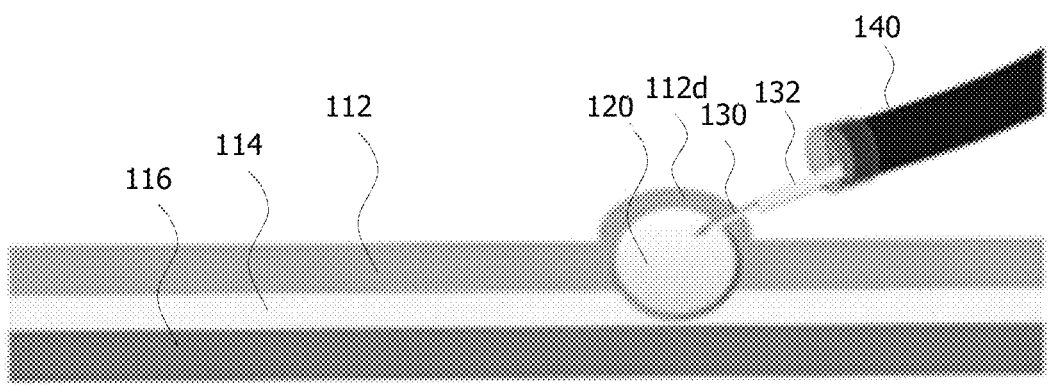

INJECTABLE COMPOSITIONS

CROSS-REFERENCE TO RELATED APPLICATIONS

This application claims the benefit of U.S. Provisional Application No. 62/365,205, entitled "INJECTABLE COMPOSITIONS" and filed Jul. 21, 2016, which is hereby incorporated by reference in its entirety.

FIELD OF THE INVENTION

This invention relates to medical articles and related methods thereof. In particular embodiments, this invention relates to injectable compositions, methods of forming the same, and related methods for performing agent-assisted procedures in, for example, a gastrointestinal (GI) tract of a patient.

BACKGROUND

An endoscope is a medical device that enables viewing of the interior of a body cavity or hollow organ without employing invasive surgical procedures. The endoscope includes a flexible elongated body (e.g., a tube) having a suitable imaging device at its distal end portion. The endoscope may be inserted through a naturally occurring opening, such as the esophagus or rectum, or through a small incision surgically made in the body. Suitable surgical instruments may be passed through the endoscope to perform various medical procedures, such as, for example, tissue sampling or removal of diseased tissue or polyps.

Endoscopic procedures are commonly used for diagnosis and/or treatment of the GI tract. For example, an endoscopic procedure may be performed to take tissue samples from the GI tract for pathological evaluation and/or therapeutic purposes. For instance, with advances in the imaging technology, endoscopic procedures may be used to accurately detect and remove pre-cancerous mucosal tissue or tumors from various locations in the GI tract.

Interventional endoscopists perform various tasks including fluid-assisted polypectomy, endoscopic mucosal resection (EMR), and endoscopic submucosal dissection (ESD) procedures to remove pre-cancerous or cancerous mucosal tissue from the GI tract. Such fluid-assisted procedures may involve injecting a fluid cushion into submucosal tissue (e.g., cushioning) or injecting a fluid between target tissue layers (e.g., dissection) so as to raise or separate the target tissue layer in order to safely perform the procedure (e.g., by preventing or reducing risks of perforating the GI tract).

SUMMARY OF THE INVENTION

In various aspects, the present disclosure provides injectable compositions suitable for performing medical procedures. In various embodiments, the injectable compositions (also referred to as injectable fluids) may comprise a suitable hydrophilic polymer having a color in the visible spectrum and water, as well as other optional components. Compositions may have color, for example, as a result of preferential reflection of incident visible light or as a result of absorption of incident radiation having first wavelength (e.g., ultraviolet or visible light) and re-emission of light having a longer wavelength in the visible spectrum (i.e., as a result of fluorescence).

In some embodiments, which may be used in combination with any of the above aspects and embodiments, the injectable compositions of the present disclosure may comprise a polysaccharide as a suitable hydrophilic polymer. For example, the polysaccharide may be selected from (a) xanthan gum and (b) hyaluronic acid and salts thereof, among other polysaccharides.

In some embodiments, which may be used in combination with any of the above aspects and embodiments, the injectable compositions of the present disclosure may comprise a hydrophilic polymer having a covalently attached dye molecule. In some of these embodiments, the dye molecule may be a reactive dye molecule.

In some embodiments, which may be used in combination with any of the above aspects and embodiments, the injectable compositions of the present disclosure may comprise a first dye molecule and a second dye molecule that is different from the first dye molecule. For example, the first dye molecule may reflect light in the visible spectrum of a first wavelength and the second dye molecule may fluoresce light in the visible spectrum at a second wavelength after being exposed to radiation having a wavelength that is shorter than the second wavelength, among other possibilities.

In some embodiments, which may be used in combination with any of the above aspects and embodiments, the injectable compositions of the present disclosure may comprise (a) a hydrophilic polymer having two or more different covalently attached dye molecules or (b) a first hydrophilic polymer having a covalently attached first dye molecule and a second hydrophilic polymer having a covalently attached second dye molecule, where the first dye molecule is different from the second dye molecule and where the first and second hydrophilic polymers may be same or different.

In some embodiments, which may be used in combination with any of the above aspects and embodiments, the injectable compositions of the present disclosure may exhibit decreasing viscosity under shear. For example, the injectable compositions may be thixotropic fluid compositions or may be pseudoplastic fluid compositions.

In some embodiments, which may be used in combination with any of the above aspects and embodiments, the injectable compositions of the present disclosure may be provided in a syringe.

In various aspects, kits may be provided which comprise (a) an injectable composition in accordance with any of the above aspects and embodiments provided in a container (e.g., a syringe) and (b) any one, any two, any three, any four, or all five of the following items: (i) an injection needle, (ii) a tissue resection device, (iii) a tissue retrieval device, (iv) an endoscope and (v) a closure device.

In various aspects, methods of performing a medical procedure in a body of a subject may be provided which comprise injecting an injectable composition in accordance with any of the above aspects and embodiments at a target site in the subject.

In some embodiments, which may be used in combination with any of the above aspects and embodiments, the sterile injectable fluid composition may be injected in the gastrointestinal tract of the subject between a first tissue layer and a second tissue layer.

In some embodiments, which may be used in combination with any of the above aspects and embodiments, the sterile injectable fluid composition may be injected at a target site within a gastrointestinal tract of the subject such that a submucosal space is created and a surface of a mucosal tissue layer protrudes into the gastrointestinal tract and such that the target site can be visualized by a difference in color between the tissue under which the submucosal space is created and surrounding tissue.

In various embodiments, which may be used in accordance with any of the above aspects and embodiments, a surgical procedure may be subsequently performed at the target site. For example, in some embodiments, the surgical procedure may include removing tissue from the target site.

In various embodiments, which may be used in accordance with any of the above aspects and embodiments, the injectable compositions may be injected using an ordinary syringe.

In further aspects, the present disclosure provides methods of forming water-soluble polysaccharides having a color in the visible spectrum. The methods comprise reacting a water-soluble polysaccharide with a dye molecule comprising one or more of the following reactive groups: a monochlorotriazine group, a monofluorochlorotriazine group, a dichlorotriazine group, a difluorochloropyrimidine group, a dichloroquinoxaline group, a trichloropyrimidine group, a vinyl sulfone group, a vinyl amide group, or a sulfonyl fluoride group.

These and other aspects, embodiments and advantages of the present invention will become immediately apparent to those of ordinary skill in the art upon review of the Detailed Description and claims to follow.

BRIEF DESCRIPTION OF THE DRAWINGS

FIG. 1 is a schematic cross-sectional view of tissue layers in the GI tract, illustrating an exemplary method of injecting an injectable composition between the mucosal and submucosal tissue layers.

DESCRIPTION OF THE EMBODIMENTS

A more complete understanding of the present invention is available by reference to the following detailed description of numerous aspects and embodiments of the invention. The detailed description of the invention which follows is intended to illustrate but not limit the invention.

According to one aspect, the present disclosure provides injectable compositions that are suitable for performing medical procedures.

In various embodiments, the compositions are sterile, for example, having been sterilized by heat, radiation or sterile filtration.

In various embodiments, the injectable compositions may comprise a suitable a hydrophilic polymer having a color in the visible spectrum (also referred to herein as a "hydrophilic polymer colorant") and water, as well as other optional agents. Because the polymer itself has color, the color does not diffuse from an injection site independent of the hydrophilic polymer, allowing the injectable compositions to be viewed at the site of injection for a period of time sufficient to perform various medical procedures at the site, such as fluid-assisted polypectomy, EMR and ESD procedures, among others.

In various embodiments, the injectable composition has a color that is readily observable (e.g., green, blue, violet, etc.) through a mucosal membrane of the gastrointestinal tract, distinct from the surrounding gastric environment, under incident visible light.

In various embodiments, the injectable composition has a color that is readily observed (e.g., green, blue, violet, etc.) through a mucosal membrane of the gastrointestinal tract, distinct from the surrounding gastric environment, upon exposure to incident radiation of a shorter wavelength than that of the color that is observed (e.g., due to fluorescence of the injectable composition upon exposure to ultraviolet light, etc.).

In various embodiments, the injectable fluid composition exhibits decreasing viscosity under shear (e.g., the injectable fluid composition may be a thixotropic fluid composition or a pseudoplastic fluid composition). Such a composition will have increased viscosity in a low shear environment (e.g., after being injected to a gastrointestinal site), while having decreased viscosity in the presence of shear (e.g., during the course of injection).

In various embodiments, the injectable compositions may comprise a hydrophilic polymer having a covalently attached dye molecule. As used herein a "dye molecule" refers to a molecule that, when covalently attached to a hydrophilic polymer, imparts a color in the visible spectrum to the hydrophilic polymer upon exposure to incident radiation, including visible radiation (i.e., visible light) and radiation having wavelengths that are shorter than that of visible light (e.g., ultraviolet radiation).

Beneficial injectable compositions for use in conjunction with the present disclosure include polysaccharides having a color in the visible spectrum. To the extent that a given polysaccharide does not possess a desired color (polysaccharides are commonly very pale or colorless), the polysaccharide may be covalently attached to a dye molecule having a desired color. By covalently attaching the dye molecule to the polysaccharide, the dye does not diffuse or "bleed" from an injection site independently of the polysaccharide.

In certain embodiments, beneficial polysaccharides for use in the present disclosure include linear polysaccharides such as cellulose, amylose, pectin, alginates, and derivatives of the forgoing, including alkyl cellulose polymers such as methyl cellulose (MC), hydroxyalkyl celluloses such as hydroxypropyl cellulose (HPC) and hydroxypropylmethyl cellulose (HPMC), and carboxyalkyl celluloses and their salts including carboxymethyl celluloses (CMC). Counterions for use in carboxyalkyl celluloses include Group I cations such as sodium and potassium, Group II cations such as magnesium and calcium, and mixtures of the foregoing.

Polysaccharides for use in conjunction with the present disclosure also include polysaccharides comprising a main chain and a plurality of monosaccharide side groups. Examples of such compounds include galactomannans which are polysaccharides having a mannose backbone with galactose side groups (e.g., a (1-4)-linked beta-D-mannopyranose backbone with branch-points from their 6-positions linked to alpha-D-galactose, i.e., 1-6-linked alpha-D-galactopyranose), such as guar gum, fenugreek gum, tara gum, locust bean gum and carob gum. Polysaccharides for use in conjunction with the present disclosure also include polysaccharides comprising a main chain and a plurality of oligosaccharide side groups (where "oligosaccharide" is defined herein as polysaccharide chains of 2, 3, 4, 5, 6, 7, 8, 9 or 10 saccharide groups), including xanthan gum. Polysaccharides further include branch-on-branch polysaccharides such as amylopectin, gum arabic, arabinoxylan, among others.

Polysaccharides for use in conjunction with the present disclosure also include glycosaminoglycans, beneficially, non-sulfated glycosaminoglycans such as hyaluronic acid and its salts, desulfated heparin, desulfated chondroitin sulfate and desulfated dermatan sulfate. Hyaluronic acid and its salts (also called hyaluronan, hyaluronate, or HA) are anionic, nonsulfated glycosaminoglycans comprising D-glucuronic acid and N-acetyl-D-glucosamine. HA is distributed widely throughout connective, epithelial, and neural tissues.

Counterions for use in hyaluronic acid salts include Group I cations such as sodium and potassium, Group II cations such as magnesium and calcium, and mixtures of the foregoing.

Chitosan, which comprises D-glucosamine and N-acetyl-D-glucosamine may also be employed as a polysaccharide.

Polysaccharides for use in conjunction with the present disclosure may vary widely in molecular weight, ranging, for example, from 5 kDa or less to 20,000 kDa or more.

Beneficial injectable fluid compositions for use in conjunction with the present disclosure include non-Newtonian fluids that exhibit decreasing viscosities under shear, including thixotropic fluids and pseudoplastic fluids. Thixotropic fluids exhibit this change as a result of time under constant shear while pseudoplastic fluids exhibit this change as a result of increasing the rate of shear stress. Such compositions will have lower viscosity in the presence of shear (e.g., during injection, thereby reducing the pressure required for a given injection rate) while having higher viscosity in a low shear environment (e.g., after being injected to a gastrointestinal site, thereby encouraging retention at the site).

Examples of thixotropic fluids for use in the present disclosure include thixotropic hydrophilic polymer colorant solutions such as thixotropic polysaccharide colorant solutions, for instance, solutions of various gums including xanthan gum or guar gum, among other suitable polymers, to which a dye molecule may be covalently attached.

Examples of pseudoplastic fluids for use in the present disclosure include pseudoplastic hydrophilic polymer colorant solutions such as pseudoplastic polysaccharide colorant solutions, for instance, solutions of glycosaminogylcans including solutions of hyaluronic acid and salts thereof and celluloses such as alkyl celluloses, hydroxy alkyl celluloses and carboxyalkyl celluloses, among other suitable polymers, to which a dye molecule may be covalently attached.

As previously indicated, in many cases, a selected hydrophilic polymer will not possess a color, as desired, in which case one or more dye molecules may be covalently attached to the polymer using a suitable covalent attachment technique. The use of multiple dyes (e.g., one dye that is directly visible at visible wavelengths and another that is visible under fluorescence) may aid visualization, depending on the imaging device that is being used.

In this regard, a wide variety of dye molecules having colors throughout the visible spectrum may be covalently attached to selected hydrophilic polymers in conjunction with the present disclosure.

Numerous dyes are known including acridine dyes, anthraquinone dyes, arylmethane dyes, diarylmethane dyes, triarylmethane dyes (including triphenylmethane dyes), azo dyes, diazonium dyes, nitro dyes, nitroso dyes, phthalocyanine dyes, quinone-imine dyes, azin dyes, eurhodin dyes, safranin dyes, indamin dyes, indophenol dyes, oxazin dyes, oxazone dyes, thiazine dyes, thiazole dyes, safranin dyes, xanthene dyes, fluorene dyes, pyronin dyes, fluorone dyes, and rhodamine dyes, among others.

In certain embodiments, fluorescent dyes may be employed, which absorb light energy of a first wavelength (e.g., ultraviolet or visible light) and re-emit light at a longer wavelength in the visible spectrum. Examples of fluorescent dyes include xanthene dyes, cyanine dyes, squaraine dyes, naphthalene dyes, coumarin dyes, oxadiazole dyes, anthracene dyes, pyrene dyes, oxazine dyes, acridine dyes, arylmethine dyes, tetrapyrrole dyes.

In some embodiments, a reactive dye may be selected for covalent attachment to a hydrophilic polymer, which reactive dye is able to react with one or more functional groups on the hydrophilic polymer. Examples of reactive dyes suitable for the present disclosure include those having one or more reactive groups, which are reactive at hydroxyl sites, such that those present in polysaccharides, including dyes comprising one or more of the following reactive groups: monochlorotriazine groups, monofluorochlorotriazine groups, dichlorotriazine groups, difluorochloropyrimidine groups, dichloroquinoxaline groups, trichloropyrimidine groups, vinyl sulfone groups, and vinyl amide groups.

In one specific embodiment, a reactive dye, for example, reactive blue 4 I (a reactive anthraquinone dye having a dichlorotriazine functional group) (λmax=595 nm) may be reacted with hydroxyl groups of a hydrophilic polymer, for example, a water-soluble polysaccharide II (hyaluronic acid is shown in the following scheme, however, essentially any hydrophilic polymer having hydroxyl groups may potentially be used) to form a hydrophilic polymer colorant, more particularly, a polysaccharide colorant III:

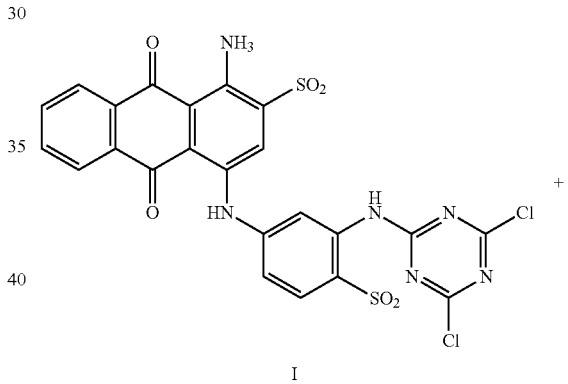

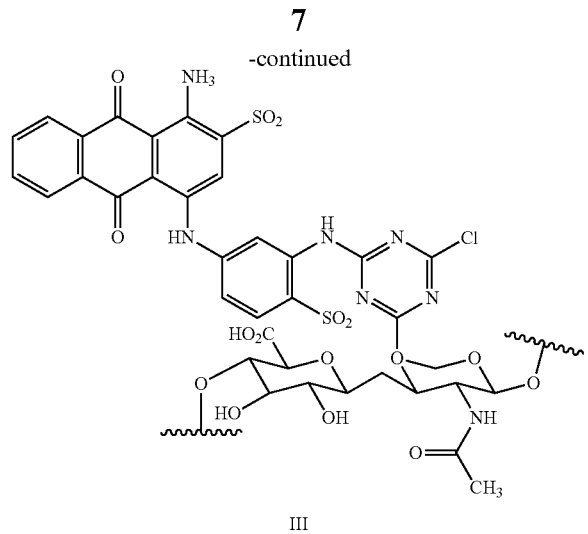

III

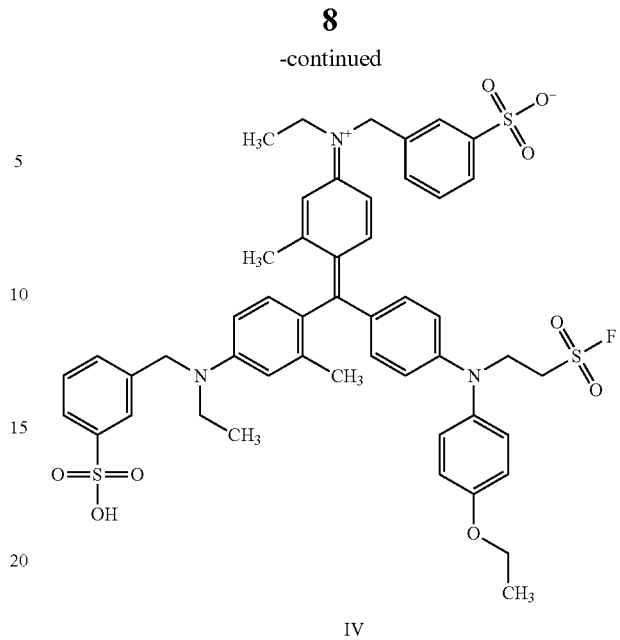

IV

In some embodiments, a dye may be covalently attached to a hydrophilic polymer via one or more additional reactive species.

In one specific embodiment, an ordinarily non-reactive dye, for example, Coomassie brilliant blue IV (a triphenylmethane dye), or another dye bearing a secondary amine group, is chemically modified by reaction with a suitable species, for example, ethylene sulfonyl fluoride V, among numerous other possible reactive species, to create a reactive dye VI (in this case, a water-soluble selective electrophile having sulfonyl fluoride groups).

Such a reactive dye may then be reacted with hydrophilic polymers having suitable nucleophilic groups such as amine groups.

In one specific example, a polysaccharide comprising N-acetyl-D-glucosamine VII (e.g., a glycosaminoglycan such as hyaluronic acid, chitosan, etc.) may be partially deacetylated to form a polysaccharide comprising D-glucosamine and residual N-acetyl-D-glucosamine groups VIII.

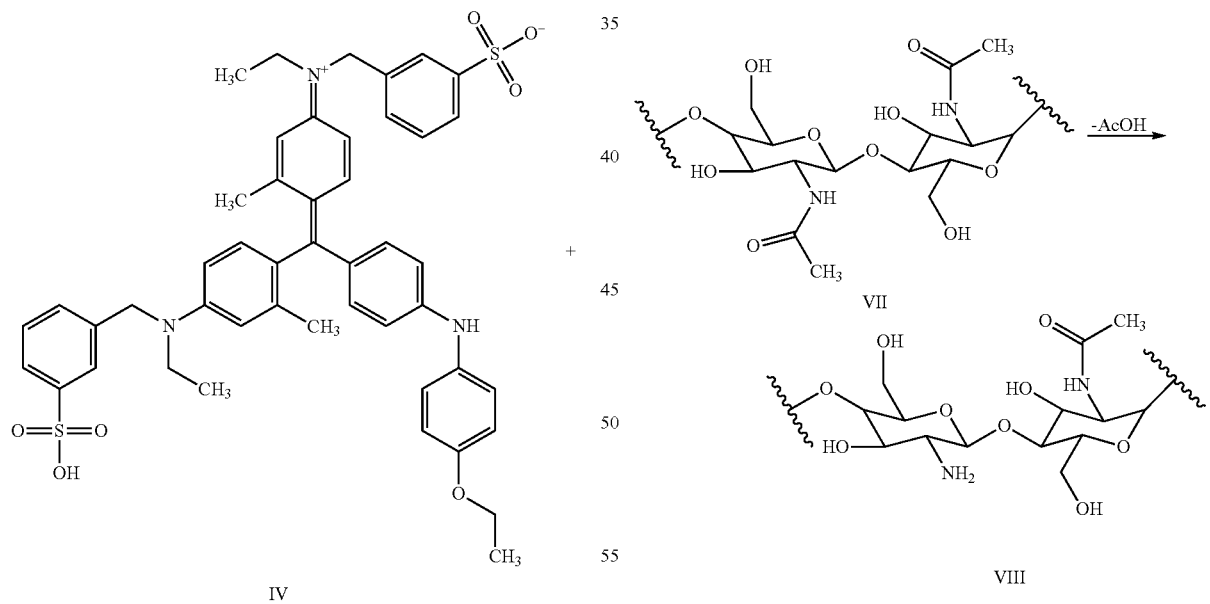

IV

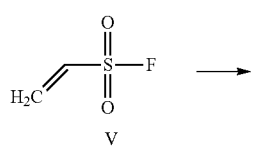

V

The polysaccharide comprising D-glucosamine and N-acetyl-D-glucosamine VIII can subsequently act as a selective nucleophile for a suitable electrophilic dye, for example, a dye having one or more sulfonyl fluoride groups, isocyanate groups including isothiocyanate groups (e.g., fluorescein isothiocyanate (FITC)), and maleimide groups (e.g., Alexa Fluor® 488 C5 maleimide), such as the reactive dye VI described above, to form a polysaccharide colorant IX:

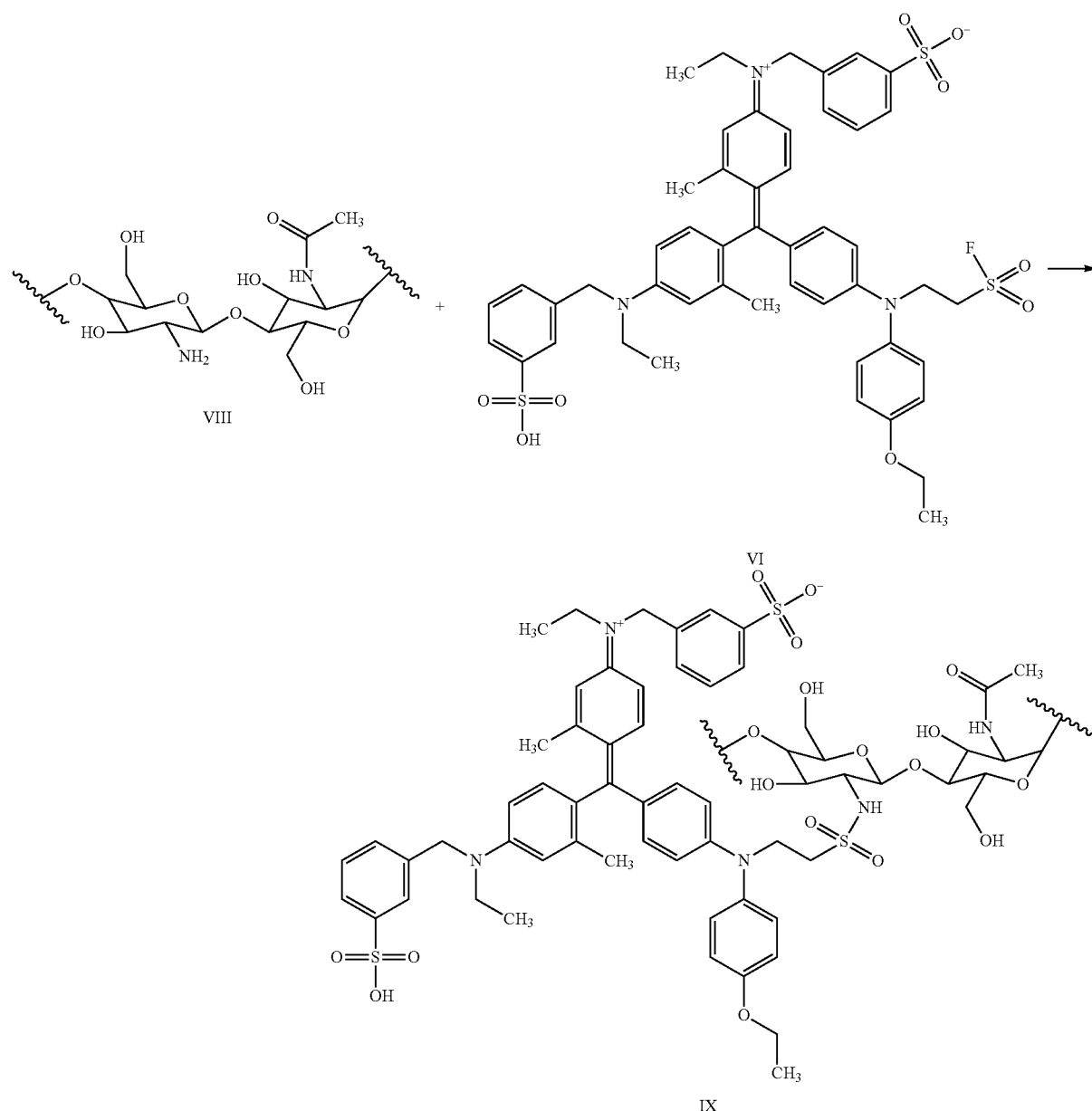

Dye molecules may be attached to hydrophilic polymers including polysaccharides by a variety of other so-called "click" reactions (i.e., high yielding reactions that are wide in scope, create byproducts that can be removed without chromatography, are stereospecific, simple to perform, and can be conducted in easily removable or benign solvents) in addition to reactions with sulfonyl fluoride, which are known in the biochemical arts.

Polysaccharide concentrations in the injectable compositions of the present disclosure may vary widely.

Addition of a given polysaccharide to water results in an increase in viscosity. Solution viscosity is a function of both the polymer concentration and the molecular weight of the polymer. At a given constant weight concentration, solution viscosity typically exhibits an exponential relationship with the molecular weight of the polymer used to adjust the viscosity of the solution. Consequently, an increase in molecular weight for a given polymer will allow a lower concentration (by weight) of the polymer to be used to achieve a given viscosity, whereas a decrease in molecular weight for a given polymer will allow a higher concentration (by weight) of the polymer to be used to achieve a given viscosity.

In some embodiments the injectable compositions for use in conjunction with the present disclosure may be colloids. As defined herein a colloid is a system that has a continuous liquid phase in which large molecules or small solid particles (e.g., particles ranging from 1 to 1,000 nm in diameter) are suspended. In various embodiments, the injectable compositions are hydrocolloids (i.e., a colloid system wherein the colloid particles are hydrophilic polymers dispersed in water).

In some embodiments, the injectable compositions consist essentially of a hydrophilic polymer colorant and water.

In some embodiments, the injectable compositions may comprise a hydrophilic polymer colorant, water and one or more additional agents.

Examples of additional agents include therapeutic agents such as cancer-treating agents (e.g., endostatin, etc.), hormones, anti-inflammatory agents, antibiotics, pain-relieving agents, antimicrobial agents (e.g., antibacterial agents, antifungal agents, etc.), coagulants, emollients, antipyrogenic agents, among other possibilities.

Further examples of additional agents include foaming agents (e.g., ammonium carbonate, azodicarbonamide). Through the use of foaming agents, the volume of fluid required to create a given volume in vivo may be reduced. For example, a foaming agent may raise tissue via steady hydrostatic forces that decrease in proportion to the surface area of the tissue exposed to the injectable composition, potentially allowing finer control of the size of the so-called "bleb" that is raised by the injectable composition.

Still further examples of additional agents include buffering agents, which may be provided in an amount sufficient to achieve an appropriate in vivo pH at the target site. Examples of suitable buffers include phosphate buffered saline (PBS), Tris (i.e., tris(hydroxymethyl)aminomethane) buffer, Tris-buffered saline, HEPES (i.e., 4-(2-hydroxyethyl)-1-piperazineethanesulfonic acid) buffer, and HEPES-buffered saline, among many others. In other embodiments, a buffer is not included in the injectable compositions of the present disclosure.

In certain embodiments, the injectable compositions of the present disclosure may be supplied in one or more syringes. Such syringes may include a barrel having an opening to receive a plunger at its proximal end and having a fitting (e.g., a luer fitting or another suitable fitting) at its distal tip for direct or indirect engagement with an injection needle such that the interior of the syringe barrel is placed in fluid communication with the interior of an injection needle. The barrel may also be provided with a flange at its proximal end for ease of engagement and a scale for determining the volume of fluid remaining in the barrel. Suitable syringe volume may range, for example, from 5 cc or less to 50 cc or more, typically from 5 cc to 15 cc.

A suitable injection needle may be provided, for example, an endoscopic injection needle that comprises a flexible tubular portion (catheter portion) having a hollow needle tip at its distal end and a suitable fitting/adaptor (e.g., a luer fitting) for engagement with a syringe barrel at its proximal end. Suitable needle gauge may vary from 20 gauge or less to 27 gauge or more, preferably 23 gauge to 25 gauge. Suitable endoscopic injection needle length may range, for example, from 200 cm to 240 cm.

In certain aspects, the present disclosure pertains to surgical procedures which employ the injectable compositions described herein. Such procedures comprise injecting an injectable fluid composition as described herein into tissue of a subject such that a surface of the tissue layer protrudes that has a color distinct from surrounding tissue, followed by performing a procedure at the injection site. While certain embodiments of the disclosure are described herein in connection with particular endoscopic procedures in the GI tract, for instance, endoscopic mucosal resection (EMR) and endoscopic submucosal dissection (ESD), embodiments of the disclosure may be used with other suitable endoscopic procedures, or for procedures other than the endoscopic procedures, such as urologic procedures, plastic surgeries, or open invasive surgeries. In addition, embodiments of the disclosure may be applied to numerous parts of a body, other than the GI tract.

EMR is an endoscopic technique developed for removal of sessile or flat neoplasms confined to the superficial layers (mucosa and submucosa) of the GI tract. EMR is typically used for removal of lesions smaller than 2 cm or piecemeal removal of larger lesions. Before the start of an EMR technique, it may be helpful to mark the margins of a targeted lesion with superficial cautery marks. The procedure starts with injection of an injectable composition into the submucosal space under the lesion, creating a "safety cushion." The cushion lifts the lesion to facilitate its removal and minimizes mechanical or electrocautery damage to the deep layers of the GI tract wall. An "inject-and-cut" technique uses submucosal injection to lift the target lesion and an electrocautery snare to remove the lesion. An "inject-lift-and-cut" technique uses submucosal injection to lift the target lesion and grasping forceps to lift the lesion and an electrocautery snare to remove the lesion. Cap-assisted EMR also uses submucosal injection to lift the target lesion after which the mucosa is suction-retracted into the cap and the lesion removed with an electrocautery snare.

ESD is typically used for en bloc removal of large (usually more than 2 cm), flat GI tract lesions. The procedure is usually done in several steps. First, the margins of the lesion may be marked by electrocautery, and submucosal injection is used to lift the lesion. Then, a circumferential incision into the submucosa is performed around the lesion with specialized endoscopic electrocautery knives. The lesion is then dissected from underlying deep layers of the GI tract wall with the electrocautery knife and removed. Various cutting devices and accessories have been developed specifically for ESD.

In each of the preceding procedures, the use of an injectable composition having a suitable color (e.g., green, blue, violet, etc.) will assist with the visualization of tissue under which a submucosal space has been formed.

Several options are available for collection of resected tissue. For example, after the cap-assisted EMR, the resected pieces can be collected into the cap and retrieved from the patient. As another example, the tissue resected during EMR or ESD can also be collected by specially designed retrieval devices (e.g., nets, baskets, etc.).

FIG. 1 is a schematic cross-sectional view of a portion of the GI tract showing the mucosal tissue layer 112, the submucosal tissue layer 114 and the muscularis propria 116, and illustrate an injection device method for performing a fluid-assisted endoscopic mucosal resection of diseased tissue 112d found in the mucosal tissue layer 112 in accordance with an embodiment of the disclosure. As shown in FIG. 1, an injection device may include an injection needle 130 with an associated catheter portion 132 that may be inserted into the GI tract by any suitable means, such as through a lumen of an endoscope 140, so that a distal end portion of the injection needle may be positioned in the vicinity of a target site. The injection needle 130 includes a hollow lumen through which the injectable composition 120 may flow. The distal end of the needle 130 may include a sharp edge configured to pierce tissue, so that the distal end of the needle 130 may be positioned at a target site between the mucosal tissue layer 112 and the submucosal tissue layer 114 in order to deliver a cushion of the injectable composition 120 between the mucosal tissue layer 112 and the submucosal tissue layer 114, lifting the mucosal tissue layer 112. The amount of injectable composition 120 to be injected may depend on various factors, such as, for example, type of procedure performed, type of resection instrument used, size of the diseased tissue 112d, and/or desired degree of cushioning. Once the injectable composition 120 is injected and a stable cushion is provided beneath the diseased tissue 112d, a suitable endoscopic resection device having a suitable cutting member (e.g., snare, knife, biopsy forceps, scissors, etc.) may be used to remove the diseased tissue 112d. As previously noted, the use of an injectable composition 120 having a suitable color will assist with the visualization of tissue under which a submucosal space has been formed.

In another aspect of the disclosure, kits useful in performing a surgical procedure are provided. The kits may include all or a subset of all the components useful for treating a patient.

The kits may include, for example an injectable composition as described herein in a form ready for injection into patient tissue (e.g., provided in one or more pre-loaded syringes) and one or more of the following (a) one or more injection needles (e.g., an endoscopic injection needle), (b) one or more tissue resection devices (e.g., snare, knife, scissors), (c) one or more tissue retrieval devices (e.g., net, basket, cap, etc.), (d) one or more combination devices such as devices having tissue injection and tissue resection functions (e.g., a needle combined with a snare), devices having tissue resection and tissue retrieval functions (e.g., a snare combined with a net, basket or cap), or devices having tissue injection, tissue resection, and tissue retrieval functions (e.g., a needle combined with a snare and a net, basket or cap), (e) an endoscope and/or (f) one or more closure devices (e.g., endoscopic clips). The kits may also include printed material with storage information and/or instructions regarding how to use the items provided within the kit, and all components may be provided in a suitable packaging material.

Although various embodiments are specifically illustrated and described herein, it will be appreciated that modifications and variations of the present disclosure are covered by the above teachings and are within the purview of the appended claims without departing from the spirit and intended scope of the invention.

The invention claimed is:

1. A sterile injectable solution comprising water and a hydrophilic polymer having a color in the visible spectrum either as a result of reflection of incident visible light or as a result of absorption of incident radiation having a first wavelength and re-emission of light having a second wavelength, longer than the first wavelength, in the visible spectrum, the hydrophilic polymer comprising a polysaccharide gum, and the sterile injectable solution exhibiting decreasing viscosity under shear, wherein the hydrophilic polymer comprises a covalently attached dye molecule.

2. The sterile injectable solution of claim 1, wherein the hydrophilic polymer comprises two or more different covalently attached dye molecules.

3. The sterile injectable solution of claim 1, wherein the sterile injectable solution comprises an additional hydrophilic polymer comprising a covalently attached additional dye molecule, wherein the dye molecule and the additional dye molecule are different, and wherein the hydrophilic polymer and the additional hydrophilic polymer are the same or different.

4. The sterile injectable solution of claim 1, wherein the dye molecule is a blue dye molecule.

5. The sterile injectable solution of claim 1, wherein the dye molecule is a fluorescent dye molecule.

6. The sterile injectable solution of claim 1, wherein the dye molecule is a reactive dye molecule.

7. The sterile injectable solution of claim 1, wherein the sterile injectable solution is a thixotropic fluid.

8. The sterile injectable solution of claim 1, wherein the sterile injectable solution is a pseudoplastic fluid composition.

9. The sterile injectable solution of claim 1, wherein the sterile injectable solution is provided in a syringe.

10. A kit comprising (a) the sterile injectable solution of claim 1 in a container and (b) any one, any two, any three, any four, or all five of the following items: (i) an injection needle, (ii) a tissue resection device, (iii) a tissue retrieval device, (iv) an endoscope and (v) a closure device.

11. A sterile injectable solution comprising water and a hydrophilic polymer having a color in the visible spectrum either as a result of reflection of incident visible light or as a result of absorption of incident radiation having a first wavelength and re-emission of light having a second wavelength, longer than the first wavelength, in the visible spectrum, the hydrophilic polymer comprising a polysaccharide gum, and the sterile injectable solution exhibiting decreasing viscosity under shear, wherein the hydrophilic polymer comprises a covalently attached dye molecule, wherein the dye molecule is a blue dye molecule, and wherein the sterile injectable solution is a pseudoplastic fluid composition.

12. The sterile injectable solution of claim 11, wherein the sterile injectable solution is provided in a syringe.

13. A sterile injectable solution comprising water and a hydrophilic polymer having a color in the visible spectrum either as a result of reflection of incident visible light or as a result of absorption of incident radiation having a first wavelength and re-emission of light having a second wavelength, longer than the first wavelength, in the visible spectrum, the hydrophilic polymer comprising a polysaccharide gum, and the sterile injectable solution exhibiting decreasing viscosity under shear, wherein the hydrophilic polymer comprises a covalently attached dye molecule and is formed by a method comprising reacting the hydrophilic polymer with a dye molecule comprising one or more of the following reactive groups: a monochlorotriazine group, a monofluorochlorotriazine group, a dichlorotriazine group, a difluorochloropyrimidine group, a dichloroquinoxaline group, a trichloropyrimidine group, a vinyl sulfone group, a vinyl amide group, or a sulfonyl fluoride group.

14. The sterile injectable solution of claim 13, wherein the sterile injectable solution is a pseudoplastic fluid composition.

15. The sterile injectable solution of claim 13, wherein the sterile injectable solution is provided in a syringe.

* * * * *